United States Patent [19]

Cook et al.

[11] Patent Number: 4,500,717

[45] Date of Patent: Feb. 19, 1985

[54] PROCESS FOR PREPARATION OF 2-OXAZOLIDINONES

[75] Inventors: Frank T. Cook; Michael O. Nutt; Hsin H. Hsieh, all of Baton Rouge, La.

[73] Assignee: The Dow Chemical Company, Midland, Mich.

[21] Appl. No.: 479,400

[22] Filed: Mar. 28, 1983

[51] Int. Cl.$^3$ ............................................ C07D 263/22
[52] U.S. Cl. .................................. 548/229; 549/512; 560/160; 564/503; 568/852
[58] Field of Search ......................... 548/229; 560/160

[56] References Cited

U.S. PATENT DOCUMENTS

| | | | |
|---|---|---|---|
| 2,437,388 | 3/1948 | Homeyer | 548/229 |
| 2,437,389 | 3/1948 | Homeyer | 548/229 |
| 2,437,390 | 3/1948 | Homeyer | 548/229 |
| 2,755,286 | 7/1956 | Bell | 548/229 |
| 2,794,013 | 5/1957 | Drechsel | 560/160 |
| 2,847,418 | 8/1958 | Steele | 260/309.7 |
| 2,977,370 | 3/1961 | Oken | 548/229 |
| 3,133,932 | 5/1964 | Horn et al. | 548/229 |
| 3,215,701 | 11/1965 | Pomot | 548/229 |
| 3,687,965 | 8/1972 | Fauran et al. | 548/229 |
| 3,703,538 | 11/1972 | Malkemus et al. | 560/160 |
| 4,062,862 | 12/1977 | Fujimoto et al. | 548/229 |
| 4,209,628 | 6/1980 | Ikeda et al. | 548/229 |
| 4,250,318 | 2/1981 | Dostert et al. | 548/229 |
| 4,272,455 | 6/1981 | Cook et al. | 548/229 |

OTHER PUBLICATIONS

Dyen, M. E. et al., Chem. Rev., 67, 197–241, (1967).
McKay, A. F. et al., J. Org. Chem., 16, 1820–1834, (1951).
Gulbins, K. et al., Chem. Ber., 93, 1975–1982, (1960).

*Primary Examiner*—Mark L. Berch
*Assistant Examiner*—S. A. Gibson
*Attorney, Agent, or Firm*—Normal L. Sims

[57] ABSTRACT

The invention is a process for the preparation of 2-oxazolidinones which comprises contacting a 2-hydroxyalkyl carbamate with an alkylene oxide or alkylene carbonate in the presence of a catalytic amount of a quaternary ammonium halide, quaternary phosphonium halide, a group I metal carbonate, hydroxide, oxide or halide, or a group II metal carbonate, hydroxide, oxide or halide under conditions such that a 2-oxazolidinone is prepared.

15 Claims, No Drawings

PROCESS FOR PREPARATION OF 2-OXAZOLIDINONES

BACKGROUND OF THE INVENTION

This invention relates to a novel process for the preparation of 2-oxazolidinones.

2-Oxazolidinones are useful as intermediates in the preparation of drugs, and polymers of 2-oxazolidinones are used, for example, in preparation of fibers, tablet coatings, lubricant additives, cigarette filters, rust inhibitors and dyeing assistants.

Many conventional processes for preparing 2-oxazolidinone and its derivatives are known. 2-Oxazolidinone may be prepared by any one of the reactions shown as follows:

the reaction of β-aminoalcohol with a compound selected from the group consisting of phosgene, dialkyl carbonate, carbon dioxide, urea, isocyanate, ethylchlorocarbonate, and carbon disulfide;

the reactions of epoxide with a compound selected from the group consisting of cyanuric acid, urea and cyanamide;

the reaction of aziridine compounds with carbon dioxide;

the reaction of acrolein with isocyanate; or the removal of hydrochloric acid from β-hydroxyalkyl semicarbazide.

However, such conventional processes have several disadvantages; for example, high cost of starting raw materials, complexity of the procedure, high toxicity of reactants or low yield of 2-oxazolidinone and its derivatives.

What is needed is a relatively simple process for the preparation of 2-oxazolidinones in high yields.

SUMMARY OF THE INVENTION

The invention is a process for the preparation of 2-oxazolidinones which comprises contacting a 2-hydroxyalkyl carbamate with an alkylene oxide or alkylene carbonate in the presence of a catalytic amount of a quaternary ammonium halide, quaternary phosphonium halide, a group I metal carbonate, hydroxide, oxide or halide, or a group II metal carbonate, hydroxide, oxide or halide under conditions such that 2-oxazolidinone is prepared.

When the 2-hydroxyalkyl carbamate is contacted with an alkylene oxide or alkylene carbonate under the conditions described, a N-(2-hydroxyalkyl)-2-hydroxyalkyl carbamate is prepared. The N-(2-hydroxyalkyl)-2-hydroxyalkyl carbamate then cyclizes to form a 2-oxazolidinone, usually under the same conditions under which it is formed. Under certain conditions, the N-(2-hyroxyalkyl)-2-hydroxyalkyl carbamate can be isolated before it cyclizes.

Another aspect of this invention is a two-step process for the preparation of 2-oxazolidinones which comprises (1) contacting a 2-hydroxyalkyl carbamate with an alkylene oxide or alkylene carbonate in the presence of a catalytic amount of a quaternary ammonium halide, quaternary phosphonium halide, a group I metal carbonate, hydroxide, oxide or halide, or a group II metal carbonate hydroxide, oxide or halide under conditions such that a N-(2-hydroxyalkyl)-2-hydroxyalkyl carbamate is prepared; and (2) cyclizing the N-(2-hydroxyalkyl)-2-hydroxyalkyl carbamate to a 2-oxazolidinone.

This invention provides a relatively simple process for the preparation of 2-oxazolidinones in high yields. This process demonstrates both high conversions of reactants and high selectivity toward the 2-oxazolidinones.

DETAILED DESCRIPTION OF THE INVENTION

The 2-oxazolidinones prepared by this process include those which correspond to formula I,

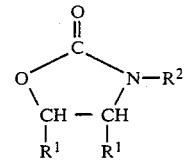

wherein $R^1$ is separately in each occurrence hydrogen, alkyl, aralkyl or aryl; and $R^2$ is separately in each occurrence hydrogen or

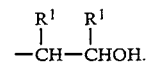

The 2-hydroxyalkyl carbamates used in this process include those corresponding to formula II

wherein $R^1$ is as defined above.

The alkylene carbonates include those which correspond to formula III

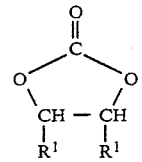

wherein $R^1$ is as defined above. Alkylene carbonates which may be used in this process include ethylene carbonate, propylene carbonate, butylene carbonate and the like.

The alkylene oxides include those which correspond to formula IV

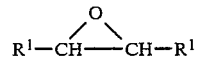

wherein $R^1$ is as defined above. Alkylene oxides which may be used in this invention include ethylene oxide, propylene oxide, butylene oxide and the like.

The N-(2-hydroxyalkyl)-2-hydroxyalkyl carbamates include those which correspond to formula V

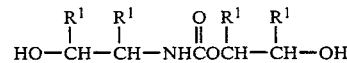

wherein $R^1$ as defined above.

$R^1$ is preferably hydrogen or alkyl, more preferably hydrogen or methyl, and most preferably hydrogen. $R^2$ is preferably hydrogen.

In the process described herein 2-hydroxyalkyl carbamate is contacted with an alkylene carbonate or alkylene oxide to prepare a N-(2-hydroxyalkyl)-2-hydroxyalkyl carbamate. The N-(2-hydroxyalkyl)-2-hydroxyalkyl carbamate cyclizes to prepare 2-oxazolidinones. This process can better be understood by reference to the following equations:

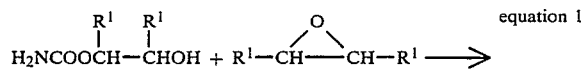

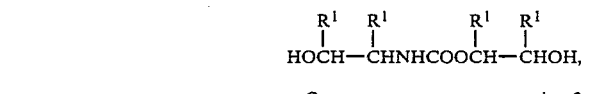

or

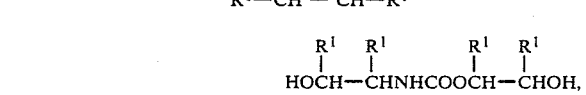

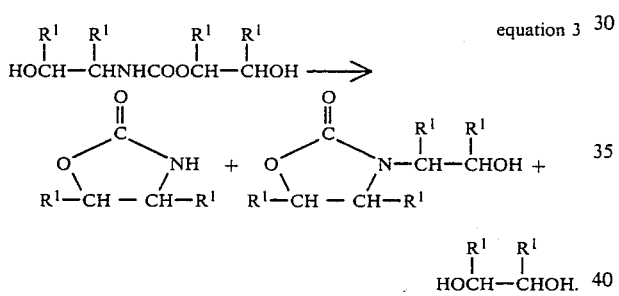

Equation 1 demonstrates the preparation of a N-(2-hydroxyalkyl)-2-hydroxyalkyl carbamate from a 2-hydroxyalkyl carbamate and an alkylene oxide. Equation 2 demonstrates the preparation of N-(2-hydroxyalkyl)-2-hydroxyalkyl carbamate from a 2-hydroxyalkyl carbamate and an alkylene carbonate. Equation 3 demonstrates the cyclization of a N-(2-hydroxyalkyl)-2-hydroxyalkyl carbamate to a 2-oxazolidinone.

Of the 2-oxazolidinones prepared by this process, the largest percentage are those wherein the nitrogen is not substituted, with a small percentage being those with a 2-hydroxyalkyl substituent. The major by-product is a glycol corresponding to the formula

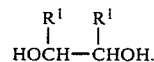

The cyclization of the N-(2-hydroxyalkyl)-2-hydroxyalkyl carbamate usually occurs under the conditions used to prepare the compound. Thus, the formation of 2-oxazolidinones and N-(2-hydroxyalkyl)-2-hydroxyalkyl carbamates usually occurs at the same time, wherein the latter compounds cyclize upon their formation to the former compounds.

Usually the reactants are contacted neat, that is without a solvent. In some embodiments, a solvent can be used but there is no advantage to doing so. There are disadvantages in that the use of solvents require costly separation and purification steps.

The reactant ratios are not critical. Between about 0.5:1 and 2.0:1 of alkylene carbonate or alkylene oxide to the 2-hydroxyalkyl carbamate is suitable. As this is a stoichiometric reaction, between about 1.05:1 and 0.95:1 is preferable to avoid wasting reactants.

The catalyst is a quaternary ammonium halide, a group I metal carbonate, hydroxide, oxide or halide; or a group II metal carbonate, hydroxide, oxide or halide. Preferred catalysts are group I metal carbonates, hydroxides, oxides or halides, with the group I metal carbonates most preferred.

Any catalytic amount of the catalyst is suitable in this process. Preferable catalytic amounts are between about 0.5 percent and about 5 percent by weight of the reactants, most preferably between about 1 percent and about 2 percent by weight of the reactants.

The temperature used can vary from 60° C. to 200° C. The temperature at which N-(2-hydroxyalkyl)-2-hydroxyalkyl carbamate cyclizes to prepare the 2-oxazolidinones is between about 85° C. and 200° C. The preferred temperature is dependent upon whether an alkylene oxide or an alkylene carbonate is reacted with the 2-hydroxyalkyl carbamate. When an alkylene oxide is used, preferable temperatures are between 100° C. and 120° C. When an alkylene carbonate is used, preferable temperatures are between 130° C. and 160° C.

This process is usually run at atmospheric pressure, although other pressures can be used.

After the contacting of the reactants has been completed, it is advantageous to continue to heat the reaction mixture to a temperature of between 85° C. and 190° C. for a period of time. This allows the cyclization of any N-(2-hydroxyalkyl)-2-hydroxyalkyl carbamate which has not yet cyclized. Further, this purifies the product as the glycol by-product boils at such temperatures and can be removed.

Advantageously, this process converts in excess of 80 percent of the 2-hydroxyalkyl carbamate to products, with a selectivity for the 2-oxazolidinones in excess of 80 percent.

The 2-hydroxyalkyl carbamates are prepared by reacting ethylene carbonate with ammonia or ammonium carbonate at room temperature.

SPECIFIC EMBODIMENTS

The following examples are included to illustrate embodiments of this invention and do not limit the scope of the invention or the claims.

EXAMPLE 1

This example illustrates the preparation of 2-oxazolidinone from ethylene oxide and 2-hydroxyethyl carbamate.

In a pressure reactor 26 g of ethylene oxide (0.59 mole) and 60 g of 2-hydroxyethyl carbamate (0.57 mole) are contacted in the presence of 1 g of potassium carbonate (0.0072 mole) at 110° C. for two hours. This resulted in an 85.3 percent conversion of 2-hydroxyethyl carbamate to products, with a selectivity to N-hydroxyethyl-2-oxazolidinone of 9.7 percent and to 2-oxazolidinone of 84.4 percent.

EXAMPLE 2

This example illustrates the preparation of 2-oxazolidinone from ethylene carbonate and 2-hydroxyethyl carbamate.

In a reactor 30 g of 2-hydroxyethyl carbamate (0.29 mole) are contacted with 25 g of ethylene carbonate (0.29 mole) in the presence of 0.6 g of potassium carbonate (0.0043 mole) at 150° C. for five hours. The reaction results in a conversion of 91 percent of the 2-hydroxyethyl carbamate with a selectivity to 2-oxazolidinone of 53 percent and N-(2-hydroxyethyl)-2-oxazolidinone of 18 percent.

What is claimed is:

1. A process for the preparation of 2-oxazolidinones which comprises contacting a 2-hydroxyalkyl carbamate with an alkylene carbonate in the presence of a catalytic amount of a quaternary ammonium halide, quaternary phosphonium halide, a group I metal carbonate, hydroxide, oxide or halide, or a group II metal carbonate, hydroxide, oxide or halide under conditions such that a 2-oxazolidinone is prepared.

2. The process of claim 1 wherein the 2-oxazolidinone corresponds to the formula

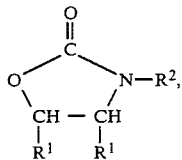

the 2-hydroxyalkyl carbamate corresponds to the formula

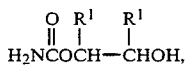

and the alkylene carbonate corresponds to the formula

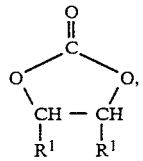

and wherein $R^1$ is hydrogen, alkyl, alkaryl or aryl; and $R^2$ is hydrogen or

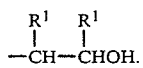

3. The process of claim 2 wherein $R^1$ is hydrogen or alkyl.

4. The process of claim 3 wherein $R^1$ is hydrogen or methyl.

5. The process of claim 4 wherein $R^1$ is hydrogen.

6. The process of claim 1 wherein the temperature is between about 85° C. and 200° C.

7. The process of claim 1 wherein the 2-hydroxyalkyl carbamate is contacted with an alkylene carbonate.

8. The process of claim 7 wherein the temperature is between about 130° C. and 160° C.

9. The process of claim 1 wherein the catalyst is a group I metal carbonate, hydroxide, oxide or halide.

10. The process of claim 9 wherein the catalyst is a group I metal carbonate.

11. The process of claim 1 wherein the carbonate is ethylene carbonate.

12. A process for the preparation of 2-oxazolidinones which comprises
   (1) contacting a 2-hydroxyalkyl carbamate with an alkylene carbonate in the presence of a catalytic amount of a quaternary ammonium halide, quaternary phosphonium halide, a group I metal carbonate, hydroxide, oxide or halide, or a group II metal carbonate, hydroxide, oxide or halide under conditions such that a N-(2-hydroxyalkyl)-2-hydroxyalkyl carbamate is prepared; and
   (2) cyclizing the N-(2-hydroxyalkyl)-2-hydroxyalkyl carbamate to a 2-oxazolidinone.

13. The process of claim 12 wherein the 2-oxazolidinone corresponds to the formula

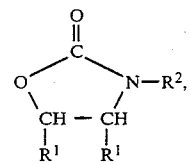

the 2-hydroxyalkyl carbamate corresponds to the formula

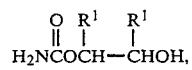

the alkylene carbonate corresponds to the formula

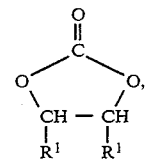

and the N-(2-hydroxyalkyl)-2-hydroxyalkyl carbamate corresponds to the formula

wherein $R^1$ is hydrogen, alkyl, alkaryl or aryl; and $R^2$ is hydrogen or

14. The process of claim 12 wherein the step 1 temperature is between about 60° C. and 200° C.

15. The process of claim 12 wherein the step 2 temperature is between about 85° C. and 190° C.

* * * * *

UNITED STATES PATENT AND TRADEMARK OFFICE
CERTIFICATE OF CORRECTION

PATENT NO. : 4,500,717

DATED : February 19, 1985

INVENTOR(S) : Frank T. Cook, Michael O. Nutt, Hsin H. Hsieh

It is certified that error appears in the above—identified patent and that said Letters Patent is hereby corrected as shown below:

In Column 1, line 56, "hyroxyalkyl" should read -- hydroxyalkyl --.

In Column 3, line 1, the line "wherein $R^1$ as defined above" should read -- wherein $R^1$ is as defined above --.

In Column 4, line 30, the word "carbamate" should instead read -- carbonate --.

Signed and Sealed this

Tenth Day of September 1985

[SEAL]

Attest:

DONALD J. QUIGG

Attesting Officer    Acting Commissioner of Patents and Trademarks - Designate